(12) United States Patent
Tabuteau

(10) Patent No.: US 8,569,328 B1
(45) Date of Patent: Oct. 29, 2013

(54) COMPOSITIONS AND METHODS COMPRISING TILIDINE OR RELATED COMPOUNDS AND DEXTROMETHORPHAN

(75) Inventor: Herriot Tabuteau, New York, NY (US)

(73) Assignee: Antecip Bioventures II LLC, Wilmington, DE (US)

( * ) Notice: Subject to any disclaimer, the term of this patent is extended or adjusted under 35 U.S.C. 154(b) by 57 days.

(21) Appl. No.: 13/478,023

(22) Filed: May 22, 2012

Related U.S. Application Data

(60) Provisional application No. 61/489,582, filed on May 24, 2011.

(51) Int. Cl.
*A61K 31/44* (2006.01)
(52) U.S. Cl.
USPC ......................................................... 514/281

(58) Field of Classification Search
USPC ......................................................... 514/281
See application file for complete search history.

(56) References Cited

U.S. PATENT DOCUMENTS

| | | | |
|---|---|---|---|
| 6,625,547 B1 * | 9/2003 | Korzekwa et al. ............... 702/22 |
| 7,659,282 B2 * | 2/2010 | Yakatan et al. ................ 514/289 |
| 2005/0031713 A1 * | 2/2005 | Ehrich et al. ................... 424/736 |
| 2008/0096872 A1 * | 4/2008 | Friedman ...................... 514/220 |

\* cited by examiner

*Primary Examiner* — Raymond Henley, III
(74) *Attorney, Agent, or Firm* — K&L Gates LLP; Louis C. Cullman; Brent A. Johnson

(57) ABSTRACT

Pain and/or neurological disorders may be treated by administering a therapeutically effective amount of dextromethorphan and a therapeutically effective amount of a compound such as tilidine that inhibits the cytochrome P450 isozyme CYP2D6, to a person in need thereof. The two compounds may be administered separately, or in a single dosage form or composition as described herein.

29 Claims, No Drawings

COMPOSITIONS AND METHODS COMPRISING TILIDINE OR RELATED COMPOUNDS AND DEXTROMETHORPHAN

CROSS-REFERENCE TO RELATED APPLICATIONS

This application claims the benefit of U.S. Provisional application No. 61/489,582, filed on May 24, 2011 under the title "PHARMACEUTICAL COMPOSITIONS COMPRISING TILIDINE AND DEXTROMETHORPHAN," which is expressly incorporated by reference herein in its entirety.

BACKGROUND

Dextromethorphan is widely used as a cough suppressant and is considered to be safe enough to be sold over the counter. Although dextromethorphan may potentiate the analgesic effect of opiates in animals, clinical studies of combinations of dextromethorphan and opiates have generally been disappointing, and have failed to demonstrate this potentiating effect in humans. Three large multicenter randomized studies failed to show any benefit from the addition of dextromethorphan to morphine. The authors concluded "[t]hese results suggest that adding the NMDA antagonist, dextromethorphan, to opioids does not add any clinical benefit" and the addition of dextromethorphan to morphine "failed to enhance opioid analgesia."

SUMMARY

Some embodiments include a pharmaceutical composition comprising a therapeutically effective amount of dextromethorphan and a therapeutically effective amount of a compound that inhibits the cytochrome P450 isozyme CYP2D6 and a pharmaceutically acceptable excipient.

Some embodiments include a method of treating pain or neurological disorders comprising administering a therapeutically effective amount of dextromethorphan and a therapeutically effective amount of a compound that inhibits the cytochrome P450 isozyme CYP2D6, to a person in need thereof.

Some embodiments include a method of enhancing the pain relieving properties of dextromethorphan, comprising co-administering dextromethorphan and a compound that inhibits the cytochrome P450 isozyme CYP2D6 with dextromethorphan.

DETAILED DESCRIPTION

Pain or neurological disorders may be treated by a method comprising administering a therapeutically effective amount of dextromethorphan and a therapeutically effective amount of a compound that inhibits the cytochrome P450 isozyme CYP2D6, to a person in need thereof.

Pain relieving properties of dextromethorphan may be enhanced by a method comprising co-administering dextromethorphan and a compound that inhibits the cytochrome P450 isozyme CYP2D6 with dextromethorphan.

These methods may be used to treat, or provide relief to, any type of pain including, but not limited to, postoperative pain, cancer pain, arthritic pain, lumbosacral pain, musculoskeletal pain, neuropathic pain, etc.

Any compound that inhibits the cytochrome P450 isozyme CYP2D6 ("CY inhibitor") may be used in conjunction with dextromethorphan. Some useful CY inhibitors may include, but are not limited to, tilidine, nortilidine, non-tilidine opioids, or metabolites thereof. In vitro studies of the metabolism of tilidine have shown that tilidine and its metabolite nortilidine inhibit certain cytochrome P450 isozymes including CYP2D6. Dextromethorphan and a CY inhibitor may be administered in separate compositions or dosage forms, or may be administered in a single composition or dosage form comprising both.

Dextromethorphan, tilidine, and nortilidine have the chemical structures shown below. Tilidine and nortilidine are typically racemic mixtures of the enantiomers depicted.

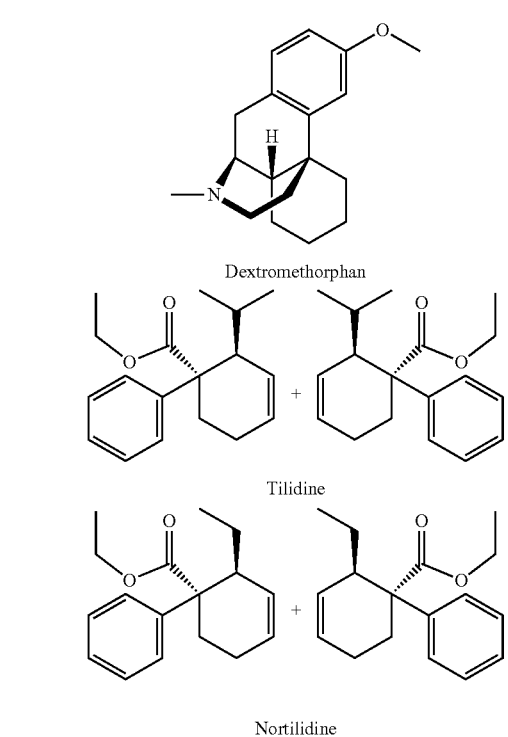

Dextromethorphan

Tilidine

Nortilidine

Unless otherwise indicated, any reference to a compound herein such as dextromethorphan or tilidine by structure, name, or any other means, includes pharmaceutically acceptable salts; alternate solid forms, such as polymorphs, solvates, hydrates, etc.; tautomers; or any other chemical species that may rapidly convert to a compound described herein under conditions in which the compounds are used as described herein.

A dosage form or a composition may be a blend or mixture of dextromethorphan and a CY inhibitor either alone or within a vehicle. For example, dextromethorphan and a CY inhibitor may be dispersed within each other or dispersed together within a vehicle. A dispersion may include a mixture of solid materials wherein small individual particles are substantially one compound, but the small particles are dispersed within one another, such as might occur if two powders of two different drugs are blended with a solid vehicle material, and the blending is done in the solid form. In some embodiments, dextromethorphan and a CY inhibitor may be substantially uniformly dispersed within a composition or dosage form. Alternatively, dextromethorphan and a CY inhibitor may be in separate domains or phases within a composition or dosage form. For example, one drug may be in a coating and another drug may be in a core within the coating.

In some embodiments, a composition or dosage form comprising dextromethorphan and/or a CY inhibitor may be substantially free of 5-[3-methylamino-prop-(E)-ylidene]-10, 11-dihydro-5H-dibenzo[a,d]cyclohepten-10-ol.

Dextromethorphan and/or a CY inhibitor, such as tilidine, nortilidine, or a metabolite thereof (all of which are referred to collectively herein as "therapeutic compounds" for convenience) may be combined with a pharmaceutical carrier selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Therapeutic compounds may be administered to a human patient in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The ratio of dextromethorphan to CY Inhibitor may vary. In some embodiments, the weight ratio of dextromethorphan to CY Inhibitor may be about 0.1 to about 10, about 0.3 to about 3, about 0.5 to about 2, about 0.8 to about 1.2, or about 1. A ratio of 0.1 indicates that the weight of dextromethorphan is 1/10 that of CY inhibitor. A ratio of 10 indicates that the weight of dextromethorphan is 10 times that of CY inhibitor. In some embodiments, the weight ratio of dextromethorphan to tilidine, nortilidine, or a metabolite thereof may be about 0.1 to about 10, about 0.3 to about 3, about 0.5 to about 2, about 0.8 to about 1.2, or about 1.

The amount of dextromethorphan in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of dextromethorphan. Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 40% (w/w) to about 50% (w/w), about 50% (w/w) to about 60% (w/w), about 70% (w/w) to about 80% (w/w), or about 80% (w/w) to about 90% (w/w) of dextromethorphan.

The amount of tilidine, nortilidine, or a metabolite thereof in a therapeutic composition may vary. For example, some liquid compositions may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of tilidine. Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of tilidine.

For compositions comprising both dextromethorphan and tilidine, some liquids may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of dextromethorphan and tilidine combined. Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of dextromethorphan and tilidine combined. In some embodiments, the weight ratio of dextromethorphan to tilidine, nortilidine, or a metabolite thereof in a single composition or dosage form may be about 0.1 to about 10, about 0.3 to about 3, about 0.5 to about 2, about 0.8 to about 1.2, or about 1.

A therapeutically effective amount of a therapeutic compound may vary depending upon the circumstances. For example, a daily dose of dextromethorphan may in some instances range from about 0.1 mg to about 1000 mg, about 20 mg to about 600 mg, about 20 mg to about 60 mg, about 60 mg to about 100 mg, about 100 mg to about 200 mg, about 200 mg to about 300 mg, about 300 mg to about 400 mg, about 400 mg to about 500 mg, or about 500 mg to about 600 mg. Dextromethorphan may be administered once daily, or twice daily or every 12 hours in amount that is about half of the daily dose.

A daily dose of a CY inhibitor such as tilidine, nortilidine, or a metabolite thereof, may in some instances range from about 10 mg to about 1000 mg, about 50 mg to about 600 mg, about 50 mg to about 100 mg, about 100 mg to about 200 mg, about 200 mg about 300 mg, about 300 mg to about 400 mg, about 400 mg to about 500 mg, or about 500 mg to about 600 mg. Tilidine may be administered once daily, or twice daily or every 12 hours in amount that is about half of the daily dose.

Therapeutic compounds may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with excipient and used in the form of ingestible tablets, buccal tablets, troches, capsules, elixirs, suspensions, syrups, wafers, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the dosage unit form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

Some compositions or dosage forms may be a liquid, or may comprise a solid phase dispersed in a liquid.

Therapeutic compounds may be formulated for parental or intraperitoneal administration. Solutions of the active compounds as free bases or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

Compositions suitable for administration by injection typically include, for example, sterile aqueous solutions or dispersions and sterile solids for the extemporaneous preparation of sterile injectable solutions or dispersions. It may be desirable for the compositions to be sterile and fluid to provide easy syringability. Some compositions may be stable under the conditions of manufacture and storage and preserved against the contaminating action of microorganisms such as bacteria and fungi. A carrier may be a solvent or dispersion medium containing, for example, water, ethanol, polyol (for example, glycerol, propylene glycol, liquid polyethylene glycol and the like), vegetable oils, or a combination thereof. Desired fluidity can be maintained, for example, by the use of a coating, such as lecithin, by the maintenance of the required particle size in the case of a dispersion, and by the use of surfactants. Prevention of the action of microorganisms may be achieved by various antibacterial and antifungal agents, for example, parabens, chlorobutanol, phenol, sorbic acid, thimerosal and the like. In many cases, it may be helpful to include isotonic agents, for example, sugars or sodium chloride. Prolonged absorption of injectable compositions may be achieved by the use of agents delaying absorption, for example, aluminum monostearate and gelatin.

Sterile injectable solutions may be prepared by incorporating therapeutic compounds in appropriate amounts in an appropriate solvent. Any other ingredients identified or disclosed herein may also be included in the solution. The solution may be sterilized by filtration or another suitable method of sterilization. Generally, dispersions may be prepared by incorporating a sterilized therapeutic compound into a sterile vehicle which contains the dispersion medium and any other appropriate ingredients identified or disclosed herein. Sterile powders or solids for the preparation of sterile injectable solutions may be prepared by methods such as vacuum drying, freeze drying, and other methods that yield a powder or solid composition comprising a therapeutic compound.

Compositions or dosage forms may be intended for sustained or immediate release, depending upon the particular need. In some embodiments, a dosage form or composition may release dextromethorphan within about 0.5 hours, about 1 hour, about 2 hours, about 3 hours, about 4 hours, or about 6 hours of administration. Some dosage forms or compositions may release a CY inibitor within about 0.5 hours, about 1 hour, about 2 hours, about 3 hours, about 4 hours, or about 6 hours of administration. Some dosage forms or compositions may release both dextromethorphan and a CY inibitor within about 0.5 hours, about 1 hour, about 2 hours, about 3 hours, about 4 hours, or about 6 hours of administration.

It may be helpful for dextromethorphan and a CY inhibitor to be released so that the relative amounts of the two compounds in a person's system are at least somewhat constant. Thus, it may be desirable for a dosage form or a composition to release dextromethorphan and a CY inhibitor at a substantially constant ratio from about the time of administration to a person until at least about 10%, about 25%, about 50%, about 75%, or about 90% of both drugs have been released from the dosage form or composition.

For immediate release dosage forms, it may be useful to avoid or limit the amount of materials that may be included to achieve sustained release. On the other hand, sustained release dosage forms may have one or more of these types of materials. Thus, in some embodiments, any of the materials identified or disclosed herein as useful for controlled or sustained release may be included in a composition or dosage form. Alternatively, a composition or dosage form may be substantially free of, or may have less than about 80% (w/w), less than about 50% (w/w), less than about 40% (w/w), less than about 30% (w/w), less than about 20% (w/w), less than about 10% (w/w), less than about 5% (w/w), less than about 2% (w/w), less than about 1% (w/w), or less than about 0.1% (w/w) of, one material, a combination of materials, or all of the materials identified or disclosed herein as useful for controlled or sustained release.

Generally, materials that have little or no solubility in water may be useful for providing sustained or controlled release of a therapeutic compound. For example, a water soluble material may quickly dissolve in physiological fluid, thus releasing any therapeutic compounds in a relatively short time, or for immediate release. By contrast, if a material has low water solubility, it may be difficult for a therapeutic compound to be released from the material because release by dissolution of the material containing the therapeutic material may be substantially slower. Sustained or controlled release dosage forms or compositions may comprise a therapeutic compound dispersed in a sustained release material, and/or a dosage form may be coated with a sustained release material. In some embodiments, a composition or dosage form may be substantially free of water insoluble solid material, or the amount of water insoluble material may be less than about 50%, less than about 40%, less than about 30%, less than about 20%, less than about 10%, less than about 5%, or less than about 1%.

Sustained or controlled release may also be obtained by use of polymeric materials which may physically entrap a therapeutic compound within its matrix. These polymers may also retain a therapeutic compound for later controlled or sustained release by non-covalent interactions such as hydrophobic interactions, hydrophilic interactions, charge-transfer, hydrogen bonding, etc., or by covalent bonding, such as by use of a hydrolysable bond like an ester.

Thus, in some embodiments, dextromethorphan, tilidine, or other therapeutic compounds may be capable of immediate release from a composition, and a composition or dosage form may be substantially free of tenacious cross-linked polymers that are capable of bonding with dextomethorphan, tilidine, and/or other therapeutic compounds; or, if a tenacious cross-linked polymer is present, the dextomethorphan, tilidine, and/or other therapeutic compound is capable of immediate release from the tenacious cross-linked polymer. Alternatively, a composition or dosage form may comprise a tenacious cross-linked polymer, as described in US20060104909, so as to provide sustained release. In some embodiments, a composition or dosage form may be substantially free of polymeric material, or the amount of polymeric material may be less than about 50%, about 40%, about 30%, about 20%, about 10%, about 5%, or about 1%.

A wax may be present in a composition or dosage form for controlled or sustained release of a therapeutic compound. A wax may include an organic material that may be insoluble in water, may be plastic or malleable near ambient temperature, and may melt above about 40° C., above about 50° C., above about 70° C., or above about 100° C. to give a low viscosity liquid. Waxes may include hydrocarbons, alcohols, esters, or carboxylic acids with long carbon chains. In some embodiments, a composition or dosage form may be substantially free of wax, or the amount of wax may be less than about 50% (w/w). Some compositions or dosage forms may be substantially free of carnuba wax or may have less than about 80%, less than about 40%, less than about 30%, less than about 20%, less than about 10%, less than about 5%, or less than about 1% (w/w) carnuba wax.

Some compositions or dosage forms for sustained or controlled release include combinations of higher aliphatic alcohols and acrylic resins. Compositions or dosage forms comprising higher aliphatic alcohols and acrylic resins may provide sustained release of therapeutically active ingredients over a period of time from five hours and for as much as 24 hours after administration, generally oral administration, in humans or animals. Some compositions or dosage forms may be substantially free of higher aliphatic alcohols and/or acrylic resins, or the amount of higher aliphatic alcohols and/or acrylic resins may be less than about 50%, less than about 40%, less than about 30%, less than about 20%, less than about 10%, less than about 5%, or less than about 1% (w/w).

Some sustained or controlled release compositions or dosage forms may comprise any pharmaceutically acceptable higher aliphatic alcohol, such as fatty alcohols of 10-18 carbon atoms, including stearyl alcohol, cetyl alcohol, cetostearyl alcohol, lauryl alcohol, myristyl alcohol and mixtures thereof. Some compositions or dosage forms may be substantially free of higher aliphatic alcohols, or the amount of any or all of these higher aliphatic alcohols may be less than about 50%, less than about 40%, less than about 30%, less than about 20%, less than about 10%, less than about 5%, or less than about 1% (w/w).

Some sustained or controlled release compositions or dosage forms may comprise any acrylic polymer which is pharmaceutically acceptable. Acrylic polymers may be cationic, anionic or non-ionic polymers and may be acrylates, including acrylic acid and acrylic acid esters, and methacrylates, including methacrylic acid or methacrylic acid esters. Functional groups may be included on acrylic polymers that make them cationic, anionic or non-ionic. For example, polymers having acrylic acid and methacrylic acid monomeric units have carboxlic acid groups that are neutral at low pH and anionic at high pH. Amine groups can be added to acrylic polymers which are neutral at high pH and cationic at low pH. Thus, acrylic polymers may be pH dependent and consequently soluble in, or resistant to solutions over a wide range in pH. Some compositions or dosage forms may be substantially free of acrylic polymers, or the amount of any or all of these acrylic polymers may be less than about 50%, less than about 40%, less than about 30%, less than about 20%, less than about 10%, less than about 5%, or less than about 1% (w/w).

Sustained or controlled release compositions or dosage forms may also include:

(a) Hydrophilic polymers, such as gums, cellulose ethers (including hydroxyalkylcelluloses and carboxyalkylcelluloses), acrylic resins and protein derived materials. A dosage form may contain between about 1% and about 80% (w/w) of at least one hydrophilic or hydrophobic polymer. Some compositions or dosage forms may be substantially free of hydrophilic polymers, gums, cellulose ethers (including hydroxyalkylcelluloses and carboxyalkylcelluloses), acrylic resins, or protein derived materials, or the amount of any or all of these materials may be less than about 1% or less than about 0.1% (w/w).

(b) Digestible, long chain ($C_{8-50}$ or $C_{12-40}$, substituted or unsubstituted hydrocarbons, such as fatty acids, fatty alcohols (including fatty aliphatic alcohols), glyceryl esters of fatty acids, mineral and vegetable oils and waxes. Some compositions or dosage forms include hydrocarbons having a melting point of between 25° and 90° C. Of these long chain hydrocarbon materials, fatty (aliphatic) alcohols may be preferred. Some compositions or dosage forms may contain up to about 60% (w/w) of at least one digestible, long chain hydrocarbon. Some compositions or dosage forms may be substantially free of digestible long chain hydrocarbon, or the amount of any or all of these long chain hydrocarbons may be less than about 50%, less than about 40%, less than about 30%, less than about 20%, less than about 10%, less than about 5%, or less than about 1% (w/w).

(c) Polyalkylene glycols. Some compositions or dosage forms may contain up to 60% (w/w) of at least one polyalkylene glycol. Some compositions or dosage forms may be substantially free of polyalkylene glycol, or the amount of polyalkylene glycol may be about 50%, less than about 40%, less than about 30%, less than about 20%, less than about 10%, less than about 5%, or less than about 1% (w/w).

Some compositions or dosage forms comprise at least one water soluble hydroxyalkyl cellulose, at least one $C_{12-36}$ or $C_{14-22}$ aliphatic alcohol and, optionally, at least one polyalkylene glycol. Some compositions or dosage forms may be substantially free of water soluble hydroxyalkyl cellulose, $C_{12-36}$ or $C_{14-22}$ aliphatic alcohol, and/or polyalkylene glycol, or the amount of water soluble hydroxyalkyl cellulose, $C_{12-36}$ or $C_{14-22}$ aliphatic alcohol, and/or polyalkylene glycol (individually or total) may be less than about 50%, less than about 40%, less than about 30%, less than about 20%, less than about 10%, less than about 5%, or less than about 1% (w/w).

In some embodiments, a hydroxyalkyl cellulose may be a hydroxy ($C_{1-6}$) alkyl cellulose, such as hydroxypropylcellulose, hydroxypropylmethylcellulose, or hydroxyethyl cellulose. Some compositions or dosage forms may contain between 1% and 45% or between 5% and 25% (w/w) of hydroxyalkyl cellulose. Some compositions or dosage forms may be substantially free of hydroxyalkyl cellulose, or the amount of hydroxyalkyl cellulose may be less than about 5%, less than about 1%, or less than about 0.1% (w/w).

Some compositions or dosage forms may include an aliphatic alcohol such as lauryl alcohol, myristyl alcohol, stearyl alcohol, cetyl alcohol, cetostearyl alcohol, etc. Some compositions or dosage forms lacking a polyalkylene glycol may contain between 20% and 50% (w/w) of the at least one aliphatic alcohol. Some compositions or dosage forms containing a polyalkylene glycol may have a combined weight of aliphatic alcohol and polyalkylene glycol of between 20% and 50% (w/w) of the total composition or dosage form. Some compositions or dosage forms may be substantially free of polyalkylene glycol and aliphatic alcohol; or may be substantially free of polyalkylene glycol and the amount of aliphatic alcohol may be less than about 20%, less than about 15%, less than about 10%, less than about 5%, or less than about 1% (w/w), or the combined weight of aliphatic alcohol and polyalkylene glycol may be less than about 20%, less than about 15%, less than about 10%, less than about 5%, or less than about 1% (w/w).

In some embodiments, a composition or dosage form may be substantially free of Dritex C (hydrogenated cottonseed oil) or has less than about 60% (w/w) Dritex C. In some embodiments, a composition or dosage form may be substantially free of Sterotex, NF (hydrogenated cottonseed oil) or has less than about 80% (w/w) Sterotex NF. In some embodiments, a composition or dosage form may be substantially free of hydrogenated cottonseed oil or has less than 60% (w/w) cottonseed oil, and may be substantially free of carnuba wax or has less than 80% (w/w) carnuba wax. In some embodiments, a composition or dosage form may be substantially free of tenacious cross-linked polymers (as defined in US20060104909, incorporated by reference in its entirety herein) or, if a tenacious cross-linked polymer is present, tilidine, nortilidine, or a metabolite thereof may be capable of immediate release from the tenacious cross-linked polymer. In some embodiments, a composition or dosage form may be substantially free of $C_{10-18}$ aliphatic alcohols or may contain less than about 50% or about 20% (w/w) $C_{10-18}$ aliphatic alcohol. In some embodiments, a composition or dosage form may be substantially free of acrylic resins or may contain less than about 20% or about 10% (w/w) acrylic resin; and may be free of hydroxypropylcellulose, hydroxypropylmethylcellulose, and hydroxyethylcellulose, or the combined amount of hydroxypropylcellulose, hydroxypropylmethylcellulose, and hydroxyethylcellulose may be less than about 10% or about 5% (w/w).

Specifically Contemplated Embodiments

The following are examples of embodiments that are specifically contemplated by the inventor:

1. A pharmaceutical composition comprising a therapeutically effective amount of dextromethorphan and a therapeutically effective amount of a compound that inhibits the cytochrome P450 isozyme CYP2D6 and a pharmaceutically acceptable excipient.
2. A method of treating pain or neurological disorders comprising administering a therapeutically effective amount of dextromethorphan and a therapeutically effective amount of a compound that inhibits the cytochrome P450 isozyme CYP2D6, to a person in need thereof.
3. A method of enhancing the pain relieving properties of dextromethorphan, comprising co-administering dextromethorphan and a compound that inhibits the cytochrome P450 isozyme CYP2D6 with dextromethorphan.
4. The method of embodiment 2 or 3, wherein the dextromethorphan and the compound that inhibits the cytochrome P450 isozyme CYP2D6 are administered in separate dosage forms.
5. The method of embodiment 4, wherein the pain comprises postoperative pain, cancer pain, arthritic pain, lumbosacral pain, musculoskeletal pain, or neuropathic pain.
6. The method of embodiment 5, wherein the pain comprises postoperative pain.
7. The method of embodiment 5, wherein the pain comprises cancer pain.
8. The method of embodiment 5, wherein the pain comprises arthritic pain.
9. The method of embodiment 5, wherein the pain comprises lumbosacral pain.
10. The method of embodiment 5, wherein the pain comprises musculoskeletal pain.
11. The method of embodiment 5, wherein the pain comprises neuropathic pain.
12. The composition or method of any one of embodiments 1-11, wherein the compound that inhibits the cytochrome P450 isozyme CYP2D6 is tilidine, nortilidine, or a metabolite thereof.
13. The composition or method of embodiment 12, wherein the compound that inhibits the cytochrome P450 isozyme CYP2D6 is tilidine.
14. The composition or method of any one of embodiments 1-11, wherein the compound that inhibits the cytochrome P450 isozyme CYP2D6 is a non-tilidine opioid.
15. The composition of any one of embodiments 1 and 12-14, wherein the composition is substantially free of 5-[3-methylamino-prop-(E)-ylidene]-10,11-dihydro-5H-dibenzo[a,d]cyclohepten-10-ol.
16. The composition of any one of embodiments 1 and 12-15, wherein tilidine is capable of immediate release from the composition, and the composition is substantially free of tenacious cross-linked polymers that are capable of bonding with tilidine.
17. The composition of any one of embodiments 1 and 12-16, wherein the composition is free of Dritex C (hydrogenated cottonseed oil) or has less than about 60% (w/w) Dritex C.
18. The composition of any one of embodiments 1 and 12-17, wherein the composition is substantially free of carnuba wax or has less than about 80% (w/w) carnuba wax.
19. The composition of any one of embodiments 1 and 12-18, wherein the composition is substantially free of Sterotex, NF (hydrogenated cottonseed oil) or has less than about 80% (w/w) Sterotex NF.
20. The composition of any one of embodiments 1 and 12-19, wherein the composition is substantially free of hydrogenated cottonseed oil or has less then 60% (w/w) cottonseed oil, and is substantially free of carnuba wax or has less than 80% (w/w) carnuba wax.
21. The composition of any one of embodiments 1 and 12-20, wherein the composition is substantially free of wax or has less than 50% (w/w) wax.
22. The composition of any one of embodiments 1 and 12-21, wherein the composition is substantially free of tenacious cross-linked polymers or, if a tenacious cross-linked polymer is present, the tilidine, nortilidine, or a metabolite thereof is capable of immediate release from the tenacious cross-linked polymer.

23. The composition of any one of embodiments 1 and 12-22, wherein the composition is a liquid or comprises a solid phase dispersed in a liquid.

24. The composition of embodiment 23, wherein the concentration of dextromethorphan is about 0.01% (w/v) to about 10% (w/v).

25. The composition of any one of embodiments 1 and 12-22, wherein the composition is a solid and the amount of dextromethorphan is at least about 10% (w/w).

26. The composition of any one of embodiments 1 and 12-25, wherein the composition is substantially free of $C_{10-18}$ aliphatic alcohols or contains less than about 50% or about 20% (w/w) $C_{10-18}$ aliphatic alcohol.

27. The composition of any one of embodiments 1 and 12-26, wherein the composition is substantially free of acrylic resins or contains less than about 20% or 10% (w/w) acrylic resin; and is free of hydroxypropylcellulose, hydroxypropylmethylcellulose, and hydroxyethylcellulose, or the combined amount of hydroxypropylcellulose, hydroxypropylmethylcellulose, and hydroxyethylcellulose is less than about 10% or 5% (w/w).

28. The composition of any one of embodiments 1 and 12-27, wherein the composition contains no water insoluble solid material, or the amount of water insoluble material is less than about 50%, 40%, 30%, 20%, 10%, or 5% (w/w).

29. The composition of any one of embodiments 1 and 12-28, wherein the dextromethorphan and the compound that inhibits the cytochrome P450 isozyme CYP2D6 are dispersed within each other or dispersed together within a vehicle.

30. The composition of any one of embodiments 1 and 12-29, wherein the dextromethorphan and the compound that inhibits the cytochrome P450 isozyme CYP2D6 are substantially uniformly dispersed within the composition.

31. A dosage form comprising a composition according any one of embodiments 1 and 12-30, wherein the dosage form releases the dextromethorphan and the compound that inhibits the cytochrome P450 isozyme CYP2D6 at a substantially constant ratio after administration to a person until at least about 50% of both drugs have been released from the dosage form.

32. A dosage form comprising a composition according any one of embodiments 1 and 12-30, wherein the dosage form releases the dextromethorphan and the compound that inhibits the cytochrome P450 isozyme CYP2D6 within about 4 hours of administration.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A pharmaceutical composition comprising a therapeutically effective amount of dextromethorphan and a therapeutically effective amount of a compound that inhibits the cytochrome P450 isozyme CYP2D6 and a pharmaceutically acceptable excipient.

2. The composition of claim 1, wherein the compound that inhibits the cytochrome P450 isozyme CYP2D6 is tilidine.

3. The composition of claim 1, wherein the compound that inhibits the cytochrome P450 isozyme CYP2D6 is a non-tilidine opioid.

4. The composition of claim 2, wherein the composition is substantially free of 5-[3-methylamino-prop-(E)-ylidene]-10,11-dihydro-5H-dibenzo[a,d]cyclohepten-10-ol.

5. The composition of claim 2, wherein tilidine is capable of immediate release from the composition, and the composition is substantially free of tenacious cross-linked polymers that are capable of bonding with tilidine.

6. The composition of claim 2, wherein the composition is free of Dritex C (hydrogenated cottonseed oil) or has less than about 60% (w/w) Dritex C.

7. The composition of claim 2, wherein the composition is substantially free of carnuba wax or has less than about 80% (w/w) carnuba wax.

8. The composition of claim 2, wherein the composition is substantially free of Sterotex, NF (hydrogenated cottonseed oil) or has less than about 80% (w/w) Sterotex NF.

9. The composition of claim 2, wherein the composition is substantially free of hydrogenated cottonseed oil or has less then 60% (w/w) cottonseed oil, and is substantially free of carnuba wax or has less than 80% (w/w) carnuba wax.

10. The composition of claim 2, wherein the composition is substantially free of wax or has less than 50% (w/w) wax.

11. The composition of claim 2, wherein the composition is substantially free of tenacious cross-linked polymers, or, if a tenacious cross-linked polymer is present, the tilidine, nortilidine, or a metabolite thereof is capable of immediate release from the tenacious cross-linked polymer.

12. The composition of claim 2, wherein the composition is a liquid or comprises a solid phase dispersed in a liquid.

13. The composition of claim 12, wherein the concentration of dextromethorphan is about 0.01% (w/v) to about 10% (w/v).

14. The composition of claim 2, wherein the composition is a solid and the amount of dextromethorphan is at least about 10% (w/w).

15. The composition of claim 2, wherein the composition is substantially free of $C_{10-18}$ aliphatic alcohols or contains less than about 50% (w/w) $C_{10-18}$ aliphatic alcohol.

16. The composition of claim 2, wherein the composition is substantially free of acrylic resins or contains less than about 20% (w/w) acrylic resin; and is free of hydroxypropylcellulose, hydroxypropylmethylcellulose, and hydroxyethylcellulose, or the combined amount of hydroxypropylcellulose, hydroxypropylmethylcellulose, and hydroxyethylcellulose is less than about 10%.

17. The composition of claim 2, wherein the composition contains no water insoluble solid material, or the amount of water insoluble material is less than about 50%.

18. The composition of claim 2, wherein the dextromethorphan and the tilidine are dispersed within each other or dispersed together within a vehicle.

19. The composition of claim 2, wherein the dextromethorphan and the tilidine are substantially uniformly dispersed within the composition.

20. A method of treating pain or neurological disorders comprising administering a therapeutically effective amount of dextromethorphan and a therapeutically effective amount of a compound that inhibits the cytochrome P450 isozyme CYP2D6, to a person in need thereof.

21. A method of enhancing the pain relieving properties of dextromethorphan, comprising co-administering dextromethorphan and a compound that inhibits the cytochrome P450 isozyme CYP2D6 with dextromethorphan.

22. The method of claim 21, wherein the dextromethorphan and the compound that inhibits the cytochrome P450 isozyme CYP2D6 are administered in separate dosage forms.

23. The method of claim 21, wherein the pain comprises postoperative pain, cancer pain, arthritic pain, lumbosacral pain, musculoskeletal pain, or neuropathic pain.

24. The method of claim 23, wherein the pain comprises postoperative pain.

25. The method of claim 23, wherein the pain comprises cancer pain.

26. The method of claim 23, wherein the pain comprises arthritic pain.

27. The method of claim 23, wherein the pain comprises lumbosacral pain.

28. The method of claim 23, wherein the pain comprises musculoskeletal pain.

29. The method of claim 23, wherein the pain comprises neuropathic pain.

* * * * *

UNITED STATES PATENT AND TRADEMARK OFFICE
CERTIFICATE OF CORRECTION

PATENT NO.         : 8,569,328 B1
APPLICATION NO.    : 13/478023
DATED              : October 29, 2013
INVENTOR(S)        : Herriot Tabuteau Page 1 of 1

It is certified that error appears in the above-identified patent and that said Letters Patent is hereby corrected as shown below:

In the Claims

In Column 13, Lines 2 and 3, "carnuba" should read --carnauba--

In Column 13, Line 10, "carnuba" appears twice and should read --carnauba--

In Column 14, Line 14, "CYP2D6, to" should read --CYP2D6 to--

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*